United States Patent [19]
Fujioka et al.

[11] Patent Number: 6,050,984
[45] Date of Patent: *Apr. 18, 2000

[54] FOLDABLE DISPOSABLE DIAPER

[75] Inventors: Yoshihisa Fujioka, Kagawa; Rumi Yamaki; Yoshio Ono, both of Kawanoe, all of Japan

[73] Assignee: Uni-Charm Corporation, Ehime, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/902,900

[22] Filed: Jul. 30, 1997

[30] Foreign Application Priority Data

Aug. 8, 1996 [JP] Japan ..................... 8-209663

[51] Int. Cl.[7] .................................. A61F 13/15
[52] U.S. Cl. ........................ 604/385.1; 604/357
[58] Field of Search ................. 604/385.1–387, 604/393–396; 607/377, 378, 379, 380, 397

[56] References Cited

U.S. PATENT DOCUMENTS

| | | | |
|---|---|---|---|
| 3,765,418 | 10/1973 | Jones, Sr. | 604/385.1 |
| 3,924,626 | 12/1975 | Lee et al. | 604/385.1 |
| 4,246,900 | 1/1981 | Schroder | 604/385.2 |
| 4,410,324 | 10/1983 | Sabee | 604/385.2 |
| 4,425,127 | 1/1984 | Suzuki et al. | 604/385.2 |
| 4,557,777 | 12/1985 | Sabee . | |
| 4,563,185 | 1/1986 | Reiter | 604/385.2 |
| 4,585,448 | 4/1986 | Enloe . | |
| 4,631,002 | 12/1986 | Lassen et al. | 604/385.1 |
| 4,690,719 | 9/1987 | Lucas | 604/385.1 |
| 5,536,350 | 7/1996 | Klemp . | |

FOREIGN PATENT DOCUMENTS

| | | | |
|---|---|---|---|
| 648068 | 10/1991 | Australia | 604/396 |
| 0157649 | 10/1985 | European Pat. Off. . | |
| 0 336 826 | 10/1989 | European Pat. Off. . | |
| 2586533 | 3/1987 | France . | |

*Primary Examiner*—John G. Weiss
*Assistant Examiner*—K. M. Reichle
*Attorney, Agent, or Firm*—Koda & Androlia

[57] ABSTRACT

A folded disposable diaper to be packed in a package while being folded inwardly about two first folding lines extending in a longitudinal direction of the diaper and then folded inwardly about two second folding lines extending in a transverse direction thereof perpendicular to the longitudinal direction. The diaper includes an absorption core having four thin areas and one thick area. The thickness of the diaper at the thin area is equal to or less than one half of the thickness of the diaper at the thick area. The first folding line is positioned outside of the center of the thin area in the transverse direction. Therefore, when the diaper is folded about the first folding lines, each of the thin areas is folded on itself to prevent an increase in the thickness of the folded diaper, while maintaining the absorbency of the absorption core.

2 Claims, 3 Drawing Sheets

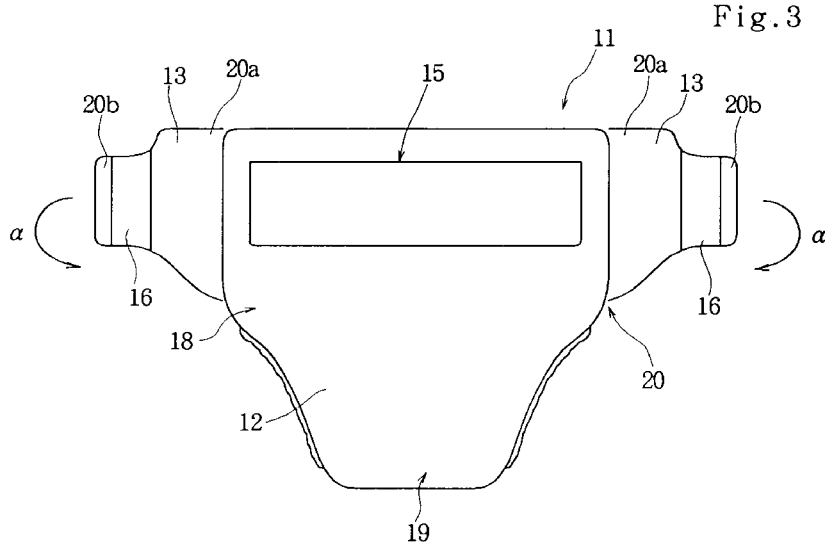

FOLDABLE DISPOSABLE DIAPER

BACKGROUND OF THE INVENTION

1. Field of the Invention

The present invention relates to a folded disposable diaper, which can be packed in a package while being folded compactly. More specifically, the present invention relates to a folded disposable diaper, which can be packed in a small package and is therefore very convenient for shipment and handy for consumers.

2. Description of the Prior Art

A disposable diaper is composed of a back sheet and a top sheet, along with an absorption core interposed between the two sheets. The back sheet faces outwardly when the diaper is worn by a wearer and comprises a resin sheet which is liquid non-permeable and air permeable. The top sheet faces toward the wearer's skin and is in contact with the wearer's skin when the diaper is worn by the wearer and comprises a non-woven fabric or a porous resin sheet which is liquid permeable. The absorption core comprises a crushed pulp or a mixture of crushed pulp and super absorbent polymers as a raw material to absorb urine passing through the top sheet.

This absorption core is prepared by pressing the raw material to have a uniform thickness and thereafter cutting the raw material into a given shape such as sandglass-like form. The resulting absorption core is then interposed between the top sheet and the back sheet and sealed therebetween. The back sheet and the top sheet are of shapes almost similar to the shape of the absorption core, but with a larger outline than the outline of the absorption core. The two sheets are bonded together at a portion where the absorption core does not exist, for example, by means of a hot-melt adhesive coated on the back sheet and the top sheet.

This disposable diaper comprises a front waist region to be applied to the abdominal area of the wearer, a crotch region to be applied to the crotch thereof, and a back waist region to be applied to the dorsal area (back area) thereof. The back sheet and the top sheet protrude at both the right and left ends of each of the front waist region and the back waist region in the width direction of the diapers, where front flaps and back flaps are formed.

Retaining fasteners consisting of attaching members and retaining members are provided to the diaper. For example, the attaching members are fixed on the ends of the back flaps in the width direction, and retaining members are fixed on the surface of the back sheet in the front waist region.

When this diaper is worn, the back flaps are wound around the wearer from the dorsal area (back area) to the abdominal area along the body outline of the wearer, to be overlaid with the front waist region. Then, the attaching members and the retaining members are attached together.

After being manufactured at a plant, the diaper is folded and packed in a package for shipping as finished goods.

In such case, the diaper is folded in such a manner that both sides of the diaper in the width direction including the front and back flaps are folded inwardly, i.e. toward the top sheet, and then the front waist region and the back waist region are overlaid onto the crotch region.

However, both sides of the diaper to be folded inwardly generally include the absorption core therein. Hence, the absorption core is overlaid to have five layers in the resulting folded state. Thus, the thickness of the diaper in the resulting folded state is disadvantageously increased and the size of a package containing a plurality of the diapers in the resulting folded state is also increased.

SUMMARY OF THE INVENTION

It is an object of the present invention to provide a folded disposable diaper which is more compact in a folded state.

It is another object of the present invention to provide a folded disposable diaper which can be folded compactly while preventing deterioration of absorbency thereof.

The present invention provides a folded disposable diaper which is packed in a package after being folded inwardly about two first folding lines extending in a longitudinal direction of the diaper and then folded inwardly about two second folding lines extending in a transverse direction thereof perpendicular to the longitudinal direction. The diaper further includes a liquid permeable top sheet, a back sheet, and an absorption core interposed between the top sheet and back sheet. The absorption core has a front waist part, a crotch part and a back waist part which in use respectively face an abdominal area, a crotch and a dorsal area of a wearer. The absorption core has an unfolded shape wherein the front waist part and the back waist part are of larger transverse dimension than the crotch part as a result of having protrusions extending in the transverse direction on transverse sides of the front waist part and the back waist part. The two first folding lines are positioned adjacent to transverse side edges of the crotch part. The absorption core has four thin areas and one thick area, and the total thickness of the thin area, the top sheet and the back sheet is equal to or less than one half of the total thickness of the thick area, the top sheet and the back sheet. Each of the thin areas includes only one of the protrusions and is separate from the other areas. The thick area includes the crotch part and extends therefrom into the front waist part and into the back waist part over the entire longitudinal dimension of the absorption core. The thin areas and the thick area each can have such boundaries that when the protrusions are folded inwardly about the two first folding lines, each of the protrusions is received against the thin area corresponding thereto and within the boundary thereof. Also, the thick area is of larger transverse dimension in the crotch part than in the front waist part and the back waist part.

BRIEF DESCRIPTION OF THE DRAWINGS

FIG. 3 is a front view of the diaper at a state when the diaper is actually worn.

DETAILED DESCRIPTION OF THE PREFERRED EMBODIMENTS

The present invention will now be described with reference to the drawings.

A diaper 11 has a laminated structure where an absorption core 14 is interposed between a back sheet 12 and a top sheet 13. The back sheet 12 is faced outwardly when the diaper 11 is worn, and comprises a resin sheet, which is liquid non-permeable and air permeable, to prevent liquid, such as urine, from oozing out of the diaper 11. The top sheet 13 to be applied to the wearer's skin and in contact with the wearer's skin in use comprises a non-woven fabric or a porous resin sheet which is liquid permeable, so that excreted urine can permeate into the absorption core 14. Further, the absorption core 14 absorbs urine permeating through the top sheet 13, and comprises a highly absorbent crushed pulp, or a mixture of a crushed pulp and a super absorbent polymer.

Figure 1A:
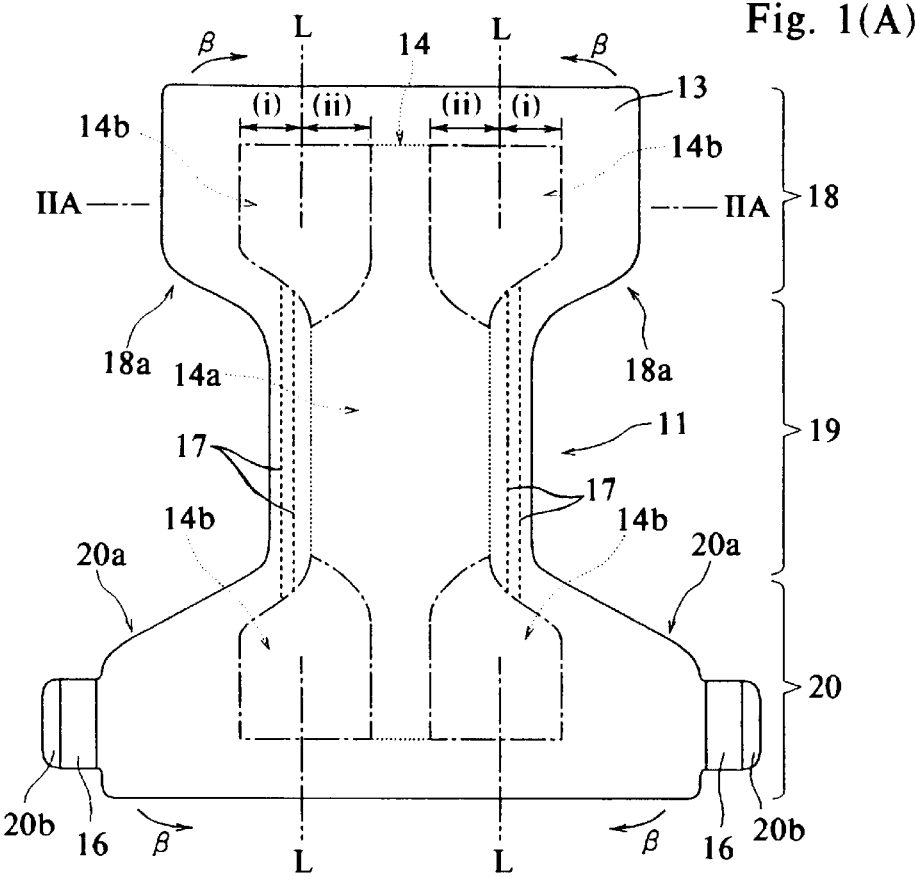
FIG. 1(A) is a plane view of an unfolded state of the folded disposable diaper of the present invention, which is viewed from the side to be applied to a wearer.

As shown in FIG. 1(A), the diaper 11 is formed in a sandglass-like form. The narrow middle region of the sandglass-like form is a crotch region 19, while the wide top end regions and the wide bottom end regions thereof are a front waist region 18 and a back waist region 20, respectively.

The absorption core 14 in the sandglass-like form is arranged from the crotch region 19 to the front waist region 18 and to the back waist region 20. In the front waist region 18 and the back waist region 20, the absorption core 14 is prepared, in the regions surrounded with an alternate long and short dash line in both the left and right regions of the diaper, as thin thickness part 14b of a thickness thinner than the thickness of the absorption core in the remaining region. In the present example, the thickness of the absorption core 14 is uniform in the region excluding the thin thickness part 14b, and so as to discriminate the region from the thin thickness part 14b, the region is designated as a thick thickness part 14a. So as to enhance the absorbency in the crotch region 19, however, the absorption core 14 positioned in the crotch region 19 may satisfactorily be thicker than the thick thickness part in the central part of the front waist region 18 and the back waist region 20.

Figure 2A:
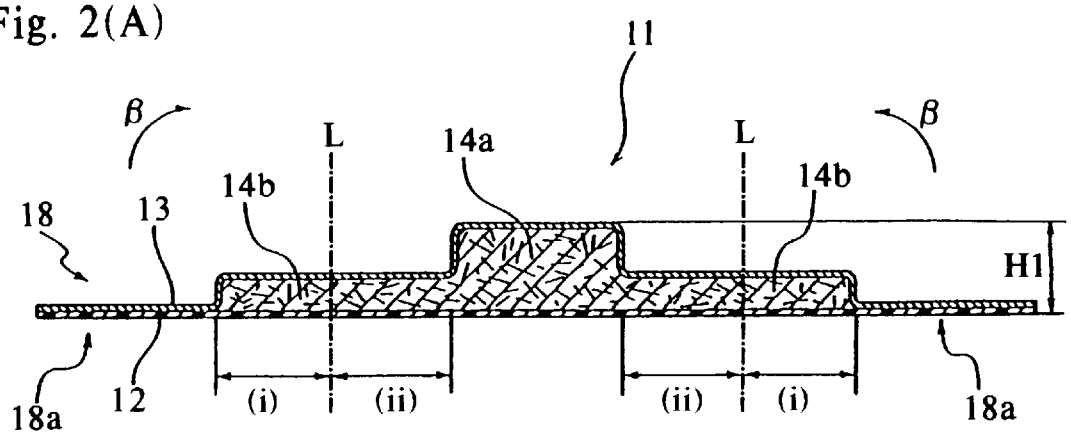
FIG. 2(A) is a cross sectional view of the diaper of FIG. 1(A) along the line IIA—IIA.

As shown in the cross sectional view of FIG. 2(A), the thickness of the diaper 11 at the thin areas 14b is equal to or less than one half of H1, which is the thickness of the diaper at the thick area 14a.

The back sheet 12 and the top sheet 13 are in a sandglass-like form, nearly similar to the form of the absorption core 14 but larger than the absorption core 14. The absorption core 14 is put in the center and interposed between the back sheet 12 and the top sheet 13. At parts where the absorption core 14 is not present between the back sheet 12 and the top sheet 13, namely at the margins in the width direction and the longitudinal direction, a hot-melt adhesive or the like is coated on the margins where the back sheet 12 and the top sheet 13 face to each other, to bond the back sheet 12 and the top sheet 13 together. In such manner, the absorption core 14 is sealed in between the back sheet 12 and the top sheet 13. The back sheet 12 and the top sheet 13 protrude in the front waist region 18 and the back waist region 20 of the diaper 11 in the width direction of the diaper 11, to form front flaps 18a and back flaps 20a.

At the end parts of the crotch region 19 in the width direction of the diaper 11 are arranged elastic members 17 elongating in the longitudinal direction of the diaper. At an elongated state between the back sheet 12 and the top sheet 13, the elastic members 17 comprising for example flat elastic braid are bonded to the back sheet 12 and the top sheet 13 by means of a hot-melt adhesive. The elastic members 17 form gatherings. When the diaper 11 is worn, the gatherings facing the thigh part of a wearer elastically press the thigh part.

Herein, the back waist region 20 of the diaper 11 is formed wider than the front waist region 18, and protrusions 20b are formed on both ends of the back waist region 20 in the width direction. Retaining fasteners 16 are fixed on the protrusions 20b, and the protrusions 20b are generally at a state folded inwardly onto the top sheet 13 of the diaper 11. When the diaper 11 is worn, the back waist region 20 is applied to the dorsal area of the wearer while the crotch region 19 is applied to the crotch thereof. Then, the diaper is folded at the crotch region 19 and the front waist region 18 is applied to the abdominal area of the wearer as shown in FIG. 3. Subsequently, the back flaps 20a are drawn forward along the body outline of the wearer toward the abdominal area. Thereafter, the retaining fasteners 16 of the protrusions 20b are fastened to another retaining fastener 15 fixed on the back sheet 12 in the front waist region 18.

Alternatively, instead of the retaining fastener 15, a film may be fixed on the surface of the back sheet 12 in the front waist region 18. Also, instead of the retaining fastener 16, an adhesive tape may be fixed on the surface of the top sheet 13 in the back waist region 20. In this case, the adhesive tape in the back waist region 20 adheres to the film in the front waist region 18 to attach the front waist region 18 and the back waist region 20 together.

Figure 1B:
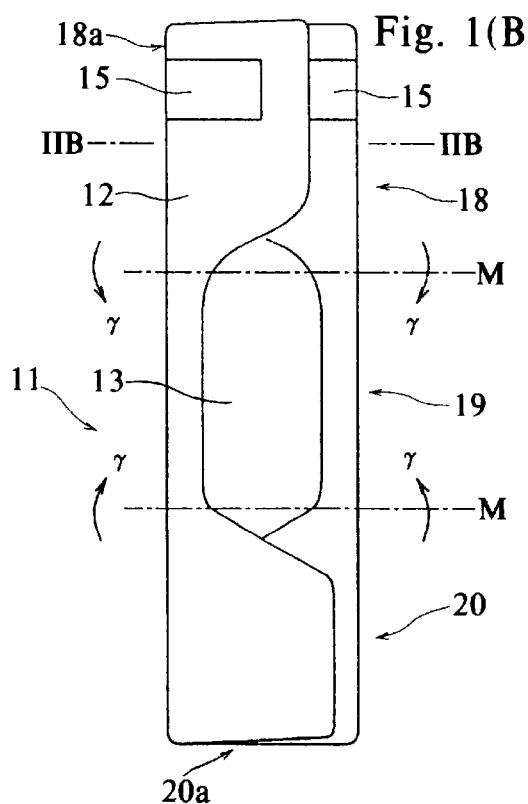
FIG. 1(B) is a plane view showing a first folded state of the diaper of FIG. 1(A), which is folded inwardly along the lines L—L.
Figure 1C:
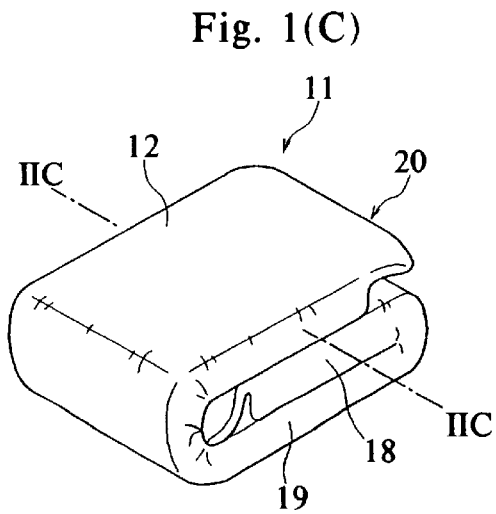
FIG. 1(C) is a perspective view showing a second folded state of the diaper, where the diaper at the first folded state shown in FIG. 1(B) is further folded inwardly along the lines M—M.

After the production of the disposable diaper 11, the front flaps 18a on both the right and left sides in the front waist region 18 as well as the back flaps 20a on both the right and left sides in the back waist region 20 are folded along the lines L—L parallel to the longitudinal direction in the direction of arrow β. As a result, the diaper 11 is folded as shown in FIG. 1(B). Furthermore, the front waist region 18 and the back waist region 20 are folded along the lines M—M parallel to the width direction of the diaper in the direction of arrow γ to be overlaid on the crotch region 19 and the diaper is folded as shown in FIG. 1(C). The diaper folded at the state shown in FIG. 1(C) is packed in a package.

Figure 2B:
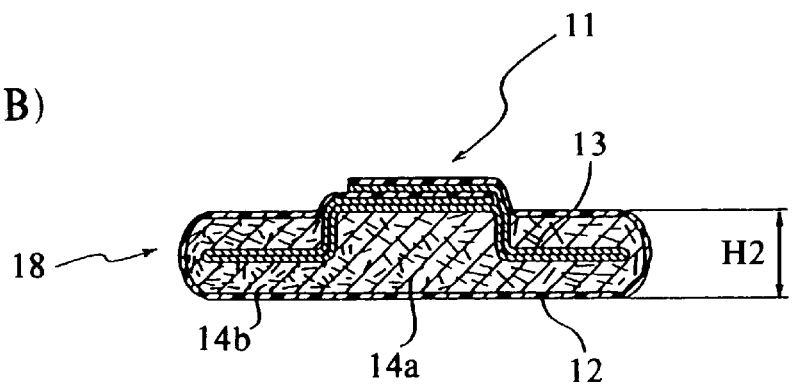
FIG. 2(B) is a cross sectional view of the diaper of FIG. 1(B) along the line IIB—IIB.

So as to make the thickness of the folded diaper 11 as thin as possible, the lines L—L should be present in a region where the absorption core 14 is not present in the crotch region 19. Furthermore, each of the lines L—L should be present outside of the center of the thin area 14b in the width direction. More specifically, when the thin area 14b is divided along the line L—L as shown in FIG. 1(A) and FIG. 2(A), the width dimension (I) of the thin area 14b is equal to or less than the width dimension (ii) of the thin area 14b. Accordingly, when the diaper 11 is folded along the lines L—L as shown in FIG. 2(B), each of the thin areas 14b is folded on itself.

Because the thickness of the diaper 11 at the thin area 14b is equal to or less than one half of the thickness H1 of the diaper 11 at the thick area 14a, the total thickness H2 of the diaper 11 where the thin area 14b is folded on itself is equal to or less than the thickness H1.

Figure 2C:
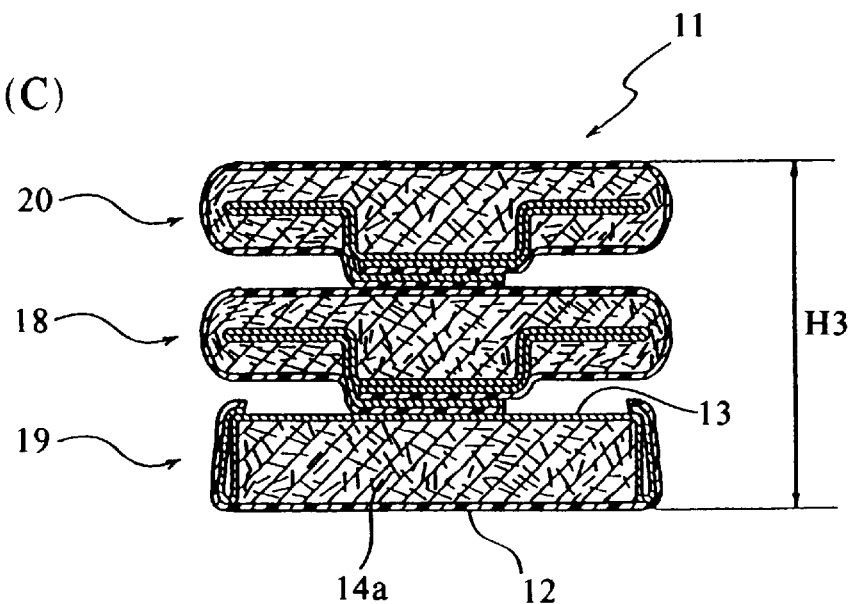
FIG. 2(C) is a cross sectional view of the diaper of FIG. 1(C) along the line IIC—IIC.

When the diaper 11 is further folded as shown in FIG. 1(C), the front waist region 18 and the back waist region 20, both folded along the lines M—M as shown in FIG. 1(B), are overlaid on the crotch region 19 as shown in the cross sectional view of FIG. 2(C). Because the total thickness H2 is equal to or less than the thickness H1 as described above, the total thickness H3 of the diaper 11 in a folded state as shown in FIG. 1(C) is the thickness of the sum of the crotch region 19, the front waist region 18 and the back waist region 20, namely 3 X H1, and the total thickness of the top sheets 13 and the back sheets 12 sandwiched therebetween.

In accordance with the present invention, therefore, the thickness of the folded diaper 11 can be suppressed to about 3-times the thickness of the diaper 11 in the unfolded state. The thickness of conventional diapers at their folded state is about 5-times the thickness of the conventional diapers in their unfolded state. When the thickness of the thick area 14*a* of the diaper 11 is the same thickness of a conventional diaper, the diaper of the present invention can be folded to about ⅗-times the thickness of a conventional diaper in its folded state. When the folded diaper of the present invention is packed in a package for shipment as a product, accordingly, the bulkiness of the product can be made less and the product can be made compact. Hence, a large number of such products can be shipped at one time, compared with conventional diapers, and the product is also handy for consumers.

Further, because the thickness of the absorption core in the crotch region is not reduced, the absorbency of the diaper is effectively maintained. Furthermore, the thickness of the absorption core in the crotch region can be more than the thickness of a conventional diaper and still the diaper of the present invention can be folded compactly compared with a conventional diaper.

The present invention has been described insofar in one example as the open-type disposable diaper. However, the present invention is not limited to the example. In accordance with the present invention, a brief-type diaper product can be made compact, by forming such thin thickness parts in the front waist region and the back waist region, whereby the thickness of the folded diaper can be made thin.

In accordance with the present invention, as has been described hereinabove, the thin thickness parts are formed in the front waist region and the back waist region of a disposable diaper to make the thickness of the folded diaper thin with no reduction of the thickness of the absorption core in the crotch region or with no loss of the absorption potency of the diaper. Thus, the diaper can be made thinner.

When the diaper of the present invention is folded and packed in a package for shipment as a product, the product can be made more compact. Compared with conventional diapers, a greater number of such products can be shipped at one time, which can contribute to the reduction of shipment cost. Because the product is not bulky, additionally, the product is handy for purchasers and consumers.

When the diaper is to be folded inwardly along a line parallel to the longitudinal direction of the diaper, furthermore, the line should be formed on each of the marginal sides in the width direction of the diaper, from the line parallel to the longitudinal line of the diaper, the parallel line dividing the thin thickness parts individually formed in the front waist region and the back waist region in halves on right and left sides, so that the area of the thin thickness parts in the inner region of the diaper, on which the end parts of the front waist region and the back waist region are overlaid, can be made larger than the area of the thin thickness parts in the front waist region and the back waist region to be folded inwardly. Hence, the thick parts of the diaper are never overlaid together to make the thickness of the folded diaper thinner.

What is claimed is:

1. A folded disposable diaper to be packed in a package, said disposable diaper being folded inwardly about two first folding lines extending in a longitudinal direction of the disposable diaper and then folded inwardly about two second folding lines extending in a transverse direction of the disposable diaper and perpendicular to the longitudinal direction, comprising:

a liquid permeable top sheet;

a back sheet bonded to said top sheet; and an absorption core interposed between the top sheet and back sheet, the absorption core having a front waist part, a crotch part and a back waist part which in use respectively face an abdominal area, a crotch and a dorsal area of a wearer, and wherein;

the absorption core has an unfolded shape wherein the front waist part and the back waist part are of larger transverse dimension than the crotch part by provision of protrusions extending in the transverse direction on transverse sides of the front waist part and the back waist part;

the absorption core has four thin areas and one thick area, and the thickness of the diaper at each of the four thin areas is equal to or less than one half of the total thickness of the diaper at the thick area;

each of the four thin areas comprising only one of the protrusions extending in the transverse direction on transverse sides of the front waist part and the back waist part and is separate from the other three of said four thin areas;

said two first folding lines are positioned adjacent and parallel to longitudinal side edges of the crotch part, said two first folding lines dividing longitudinally respective pairs of each of said four thin areas substantially in half;

said thick area is a thickest area of said absorption core;

the thick area includes the crotch part and extends therefrom into the front waist part and into the back waist part over the entire longitudinal dimension of the absorption core;

said two second folding lines are positioned respectively longitudinally on each side of the crotch part and extend transversely to said longitudinal direction of said disposable diaper;

the thin areas and the thick area have such boundaries that when the protrusions are folded inwardly about said two first folding lines, each of the protrusions is received against the thin area corresponding thereto and within the boundary thereof; and the thick area is of larger transverse dimension in the crotch part than in the front waist part and the back waist part.

2. A folded disposable diaper according to claim 1, wherein when the absorption core is folded about said two first folding lines, the absorption core has a generally rectangular shape.

\* \* \* \* \*

UNITED STATES PATENT AND TRADEMARK OFFICE
CERTIFICATE OF CORRECTION

PATENT NO.   : 6,050,984
DATED        : April 18, 2000
INVENTOR(S)  : Yoshihisa Fujioka, et al.

It is certified that error appears in the above-indentified patent and that said Letters Patent is hereby corrected as shown below:

On the Title Page:
Item [75] Inventors:   Change "Yoshihisa Fujioka, Kagawa; Rumi Yamaki; Yoshio Ono, both of Kawanoe, all of Japan," to --Yoshihisa Fujioka, Kagawa; Rumi Yamaki; Yoshio Ono, both of Ehime, all of Japan--

Signed and Sealed this

Twenty-seventh Day of March, 2001

*Attest:*

NICHOLAS P. GODICI

*Attesting Officer*   Acting Director of the United States Patent and Trademark Office